United States Patent [19]

Knepper

[11] Patent Number: 4,812,448

[45] Date of Patent: Mar. 14, 1989

[54] METHOD FOR THE PREVENTION OF OCULAR HYPERTENSION, TREATMENT OF GLAUCOMA AND TREATMENT OF OCULAR HYPERTENSION

[76] Inventor: Paul A. Knepper, 175 E. Delaware St., Chicago, Ill. 60611

[21] Appl. No.: 918,480

[22] Filed: Oct. 14, 1986

Related U.S. Application Data

[63] Continuation-in-part of Ser. No. 663,507, Oct. 22, 1984, Pat. No. 4,617,299, which is a continuation-in-part of Ser. No. 562,843, Dec. 19, 1983, abandoned.

[51] Int. Cl.$^4$ .......................................... A61K 31/595
[52] U.S. Cl. .................................. 514/178; 514/913; 514/974
[58] Field of Search ............... 514/178, 453, 913, 974

[56] References Cited

PUBLICATIONS

"Steroids"—Fieser et al., p. 519-1959.
Modern Drug Encyclopedia (1975), pp. 577, 578, 579 & 780.
Lamble, J. W. and Lamble, A. P., "Some Effects of Progestogens, Oestrogens and Androgens on the Ocular Tension of Rabbits and Owl Monkeys"; *Exp. Eye Res.*, vol. 26, pp. 599-610 (1978).
Armaly, M. F., M.D.; "Effect of Corticosteroids on Intraocular Pressure and Fluid Dynamics", *Archiv. of Ophthalmol.*, vol. 70, pp. 492-497 (1963).
Dorsch, M.D., William and Thygeson, M.D., Phillip; "The Clinical Efficacy of Medrysone, a New Ophthalmic Steroid", *Amer. Jour. Ophthalmol.*, vol. 65, No. 1, pp. 74, 75 (1968).
Godel, Regenbogen and Stein; "On the Mechanism of Cortico Steroid Induced Ocular Hypertension"; *Annals of Ophthal.*, pp. 191-196 (1978).
Treister and Mannor, "Intraocular Pressure and Outflow Facility Effect of Estrogen and Combined Estrogen-Progestin Treatment in Normal Human Eyes"; *Arch. Ophthal.*, vol. 83, pp. 311-318 (1970).
Meyer, Roberts, Liebowitz, McGowan and Honle; "Influence of Norethynodrel with Mestranol on Intraocular Pressure in Glaucoma"; *Arch. Ophthal.*, vol. 75, pp. 771-773 (1966).
Meyer, Leibowitz, Christman, Niffenegger; "Influence of Norethynodrel with Mestranol on Intraocular Pressure in Glaucoma"; *Arch. Ophthal.*, vol. 75, pp. 157-161 (1966).
Cantrill, Palmberg, Fink, Waltman, Podos and Becker; "Comparison of an In Vitro Potency of Corticosteroids with Ability to Raise Intraocular Pressure"; *Amer. Jour. Opthal.*, vol. 79, No. 6, p. 1012 (1975).

*Primary Examiner*—Douglas W. Robinson
*Attorney, Agent, or Firm*—Dressler, Goldsmith, Shore, Sutker & Milnamow, Ltd.

[57] ABSTRACT

A novel pharmacologic therapy for treatment of idiopathic primary open angle glaucoma, drug-induced glaucoma and elevated intraocular pressure is disclosed. The pharmacologic therapy consists of a novel composition comprised of 17-alpha-methyl-testosterone and a physiologically tolerable carrier. In accordance with a method aspect of this invention, the active ingredient is administered to the eye of a warm blooded animal in such a manner as to maintain physiologic or normal intraocular pressure, or to return elevated intraocular pressure to normal levels. The method aspect of this invention may also be employed to ameliorate drug induced elevated intraocular pressure.

9 Claims, No Drawings

METHOD FOR THE PREVENTION OF OCULAR HYPERTENSION, TREATMENT OF GLAUCOMA AND TREATMENT OF OCULAR HYPERTENSION

CROSS REFERENCE TO RELATED APPLICATION

This is a Continuation-In-Part of co-pending application Ser. No. 663,507 filed Oct. 22, 1984, now U.S. Pat. No. 4,617,299, which application, in turn, is a Continuation-In-Part of application Ser. No. 562,843 filed Dec. 19, 1983, now abandoned.

TECHNICAL FIELD OF THE INVENTION

The present invention relates to regulation of intraocular pressure, and more particularly to a novel composition and method for prevention or reduction of elevated intraocular pressure such as found in glaucoma by the use of corticosteroid anti-inflammatory agents.

BACKGROUND OF THE INVENTION

Glaucoma is one of the leading causes of irreversible blindness. Although the occurrence of glaucoma is more frequent in the elderly, the disease affects all age groups. Glaucoma is a significant cause of visual impairment and results in significant loss of productivity in affected individuals. Glaucoma is not a single disease process, although it may simply be characterized as a condition where the intraocular pressure (IOP) is too high for the normal functioning of the optic nerve. Damage to the optic nerve is associated with progressive loss of visual field, and if untreated can lead to total irreversible blindness.

As the term glaucoma encompasses several disease states, the causes of glaucoma are many. This invention is directed toward the treatment of one class of glaucoma, primary open angle glaucoma, where there is a normal anterior chamber and an open anterior chamber angle. This disease state may occur spontaneously or may be secondary to treatment for another systemic or ocular disease state. An example of the latter is elevated intraocular pressure secondary to corticosteroid treatment for inflammation.

The administration of corticosteroid ocular anti-inflammatory agents has been linked to elevated intraocular pressure in the human eye [Armaly, Arch. Ophth. 70:482 (1963); Becker et al., Arch. Ophthal. 70:500 (1963); Nicholas, Arch. Ophthal. 72:189 (1964); Armaly, Arch. Ophthal. 70:492 (1963)]. Corticosteroid therapy for systemic inflammation may also induce elevated intraocular pressure. These compounds also are commonly administered to relieve ocular inflammation. However, elevated intraocular pressure can be observed when a member of the class of corticosteroids is topically administered to normal and glaucomatous eyes. [Cantrill, et al., Am. J. Ophthal. 79:6:1012 (1975)]. The pressure elevating effect of topically applied corticosteroids has been successfully reproduced in rabbits [Levene, et al., Am. J. Ophthal. 78:3:509 (1974); Bonomi, et al., Graefes Arch. Ophth. 209:73 (1978); Podos, Symp. on Eye Dis. 81:632 (1976); Knepper, et al., Exp. Eye Res. 27:567 (1978)].

Specifically, the topical instillation of dexamethasone, (9-alpha-fluoro-16-methyl prednisolone) to the eye results in a condition similar to glaucoma; that is, elevation of intraocular pressure (IOP) in man. This undesirable side effect of corticosteroid treatment, if unchecked, may result in permanent debilitating effects upon the eye. These undesirable effects include visual field loss or other impairment of visual acuity resulting from optic nerve damage. These effects are similar to those seen in idiopathic primary open angle glaucoma. The similarity of corticosteroid induced glaucoma to idiopathic primary open angle glaucoma, coupled with the reproducible effects of corticosteroid dexamethasone-induced glaucoma in the rabbit, indicate that dexamethasone-induced glaucoma is a good model of human primary open angle glaucoma as well as corticosteroid induced glaucoma.

A. Open Angle Glaucoma

Primary open angle glaucoma is the most common form of glaucoma. It is a major cause of blindness. Primary open angle glaucoma is characterized by elevated intraocular pressure which, if untreated, irreversibly damages the optic nerve. This results in impairment of visual field or loss of some or all of the affected individuals vision. Several researchers in the field have suggested that primary open angle glaucoma is caused by alteration in cortisol metabolism in the cells of the trabecular meshwork [Southren et al., Invest. Ophthal. 24:1413 (1983)]. While the exact mechanism causing glaucoma is unknown, the physiologic effect of elevated intraocular pressure is found in spontaneous primary open angle glaucoma and corticosteroid induced open angle glaucoma. Spontaneously occurring primary open angle glaucoma is physiologically similar to the untoward intraocular pressure elevating side effect of corticosteroid administration.

The conventional therapeutic regime for primary open angle glaucoma or ocular hypertension typically includes topical administration of pilocarpine, epinephrine, anti-cholinergic agents and beta-adrenergic blocking agents administered alone or in combination. These drugs are believed to decrease the amount of aqueous humor formed by the eye, or decrease the resistance of aqueous humor drainage out of the eye, or both. The result is a decrease in intraocular pressure.

Unfortunately, the conventional therapies are often of limited success. Side effects of these therapies include blurred vision, irritation of the cornea and conjunctiva, and cataract formation. [Goodman and Gilman, The Pharmacological Basis of Therapeutics, 4th Ed., MacMillan Pub. (1970); Shields, A Study Guide for Glaucoma, Williams & Wilkins Pub. (1982)]. Untoward systemic side effects also occur with the conventional therapies.

Carbonic anhydrase inhibitors in tablet form may be added to the treatment regime should the topical administration of the above-mentioned drugs be poorly tolerated or fail to reduce intraocular pressure [Shields, supra]. Unfortunately, carbonic anhydrase inhibitors present further opportunities for untoward side effects, such as drowsiness, parasthesia, renal calculi, bone marrow depression, and various allergic reactions.

Surgical intervention is recommended only where the maximum tolerable medical therapy fails to halt the progressive glaucomatous damage to the optic nerve resulting from elevated intraocular pressure. In these cases, surgery may be required due to medical failure of pharmacologic agents as a result of progressive glaucomatous damage to the optic nerve, drug intolerance, poor patient compliance with treatment regimes, or unsuccessful utilization of all forms of anti-glaucoma drugs. Surgery is attempted to create an alternative pathway for aqueous humor drainage or to laser-treat the trabecular meshwork (the aqueous humor filter). The long term success of surgical intervention is not uniform among patients so treated. Futhermore, the administration of anti-glaucoma agents is a life-long therapeutic regime with unknown ultimate ocular or systemic side effects that may result from the duration of treatment, combination of agents employed, drug interactions or acquired sensitivities to conventional anti-glaucoma preparations.

B. Risk Factors

Members of the population at risk for acquiring primary open angle glaucoma, the most common form of glaucoma, may present one or several risk factors. The incidence of primary open angle glaucoma increases with every advancing decade. There is a higher prevalance of the disease in males.

The onset of primary open angle glaucoma can be related to systemic disease states such as diabetes mellitus, Cushings syndrome, hypothyroidism, hemodynamic crises, hyper-coagulation disorders and alterations in systemic blood pressure. Close relatives of patients with primary open angle glaucoma are at a significantly higher risk than the general population according to several studies [Kolken et al., Israel J. Med. Dir. 81:357 (1972); Cameron et al., *Glaucoma*, LB Hunt Ed., Edinburgh (1966); Shin et al., Arch. Ophthal. 95:598 (1977)]. Inheritance of a tendency to acquire glaucoma is believed to be by a polygenic, multifactorial mode. High myopes present an increased risk of disease [Schlossman, Intraocular Lens Med. J. 1:84 (1975)], although the relationship between myopia and glaucoma may be indicative of a longer period of onset or early glaucoma rather than truly higher intraocular pressure distribution throughout the myopic population.

Persons receiving corticosteroid therapy often acquire elevated introcular pressure subsequent to that therapy. Corticosteroid therapy places individuals at high risk for subsequent development of elevated intraocular pressure with subsequent glaucomatous symptomology. (Shields, supra.)

Other drug therapies may cause increased intraocular pressure as well. Thus ACTH, glucocorticoids and growth hormone may cause a secondary elevation of intraocular pressure. Hypothyroidism also has been associated with glaucoma.

A reproducible correlation between topical corticosteroid therapy and elevated intraocular pressure has been established. Elevated intraocular pressure is one of the major adverse side effects of corticosteroid treatment for systemic or ocular disease states. (Shields, supra; Goodman and Gilman, supra).

Many primary open angle glaucoma patients and ocular hypertensives suffer even greater elevation of intraocular pressure when topical corticosteriods are administered as anti-inflammatory agents. A positive correlation between the administration of corticosteriods such as dexamethasone resulting in elevated intraocular pressure has been established. [Armaly, Arch. Ophthal. 70:492 (1963); Godel et al., Ann. Ophthal. 3:191 (1978); Cantrill et al., Am J. Ophthal. 79:6:1012 (1975); Shields, supra].

C. Induced Elevated Intraocular Pressure

Corticosteriod glaucoma in humans (secondary glaucoma) closely resembles the spontaneous disease state of primary open angle glaucoma. Animal models of this disease state have been successfully obtained through the topical instillation of glucocorticoids and corticosteroids such as dexamethasone [Knepper et al., Exp. Eye Res. 27:567 (1978)]. Rabbits are the primary experimental animals of choice because of similarities to humans in physiology of aqueous humor dynamics, the ready availability of the animals, and suitability for accurate tonometry [Bonomi, Graefes Archiv. Ophthal. 209:73 (1978)].

Successful induction of increased intraocular pressure in the rabbit has been accomplished by a number of researchers utilizing corticosteroids. This has resulted in the conclusion that the rabbit is a good model of corticosteriod induced glaucoma, and that this induced disease state is a good model for investigation of treatment regimes as applied to human primary open angle glaucoma [Bonomi, Graefes. Arch. Ophth. 209:73 (1978); Levene, Am. J. Ophthal. 78:3:509 (1974); Southren et al., Invest. Ophthal. 15:3:222 (1976); Knepper et al., Exp. Eye Res. 27:567 (1978); Podos, Symp. on Eye Dis. 81:632 (1976)]. A variety of routes of administration of corticosteriods produce elevated IOP such as is seen in primary open angle glaucoma; however, topical application to the eye is particularly effective in increasing intraocular pressure.

Reduction of corticosteroid induced elevated intraocular pressure in the rabbit provides an excellent model for treatment of the disease state in humans. This treatment can be accomplished by a repeated application of a composition containing 17-alpha-methyl-testosterone.

Lamble et al., Exp. Eye Res. 26:599–610 (1978), describe the effects or progestogens, estrogens and androgens on the ocular tension in rabbits and owl monkeys, and reports that androgens and estrogens were found not to exert hypotensive effects in the eyes of either species that present normal intraocular pressure. Lamble et al. specifically report that a one-time administration of testosterone and methyltestosterone as 0.1 weight percent suspensions were observed to have no ocular hypotensive effect.

It has now been found, however, that 17-alpha-methyl-testosterone when administered for an extended time period to an eye having elevated intraocular pressure does indeed have an ocular hypotensive effect.

SUMMARY OF THE INVENTION

The present invention contemplates a method for reducing elevated intraocular pressure in an eye of a warm blooded animal. This method comprises contacting the eye, continuously or repeatedly at predetermined intervals, with an effective amount of 7-alpha-methyl-testosterone for a time period of at least about three days.

An aspect of the present invention also contemplates administration of 17-alpha-methyl-testosterone to the eye substantially concurrently with the administration to the warm blooded animal of an intraocular pressure elevating substance, such as a corticosteroid, so as to minimize or obviate the effects of the latter substance on the eyes of animal receiving the same.

In accordance with the present invention, 17-alpha-methyl-testosterone is administered to the eye of the warm blooded animal preferably in a unit dose in the range of about 0.001 milligrams to about 10 milligrams per administration, the more preferred unit dose being in the range of about 0.004 to about 4 milligrams per administration, for a time period of at least about three days.

DETAILED DESCRIPTION OF THE INVENTION

The following definitions apply to the terms set forth below as used herein:

Anabolic Agent: A composition that promotes storage of protein and generally stimulates tissues.

Androgenic Agent: An agent that influences and promotes the male secondary sex characteristics.

Glaucoma: A group of disease states characterized by elevated intraocular pressure, cupping of the optic nerve and/or visual field loss.

Pathogenic Intraocular Pressure: Intraocular pressure of about 21 mm of mercury, or greater, as measured by Schiotz, MacKay-Marg or applanation tonometry.

Physiologic Intraocular Pressure: Intraocular pressure that is less than about 20 mm mercury when measured by standard tonometric techniques; also referred to as normal intraocular pressure.

Primary Glaucoma: Forms of glaucoma that are not consistently associated with obvious systemic or other ocular disorders that might account for the alteration in outflow resistence.

Primary Open Angle Glaucoma: A disease state occurring in eyes presenting a deep anterior chamber and an open anterior chamber angle. The mechanism for alteration of the outflow resistance is unknown.

Secondary glaucoma: Characterized by associated ocular or systemic abnormalities that appear to be responsible for the alteration in resistence to aqueous outflow. In the detailed description of the invention, these conditions may be induced by intraocular pressure elevating pharmacologic therapies. (drug induced glaucoma).

Tonometry: Generally, the procedure utilized to measure the intraocular pressure by relating the deformation of the globe to the force responsible for the deformation. The two basic types of tonometers are indentation tonometers, wher the shape of the deformation is a truncated cone (Schiotz tonometer), and applanation tonometers. Applanation tonometers create a deformation by a simple flattening. The shape of the deformation is constant allowing simple mathematical formulae to be utilized for calculation. The three types of applanation tonometers are (a) Variable force—this type measures the force required to flatten a standard area of the corneal surface (Goldman applanation; Mackay-Marg tonometer).

(b) Variable area—measures the area of the cornea flattened by a known force (Maklakov tonometry).

(c) Time—this type of tonometer measures the amount of time required to deform the cornea in response to a standard force, e.g., a puff of air (non-contact tonometer).

Unit Dose: As used herein, this term refers to physically discrete units suitable as unitry dosages for human patients and other warm blooded animals, each unit containing a predetermined quantity of the active ingredient calculated to produce the desired therapeutic effect in association with the required physiologically tolerable carrier, e.g. a diluent or a vehicle.

The specifications for the novel unit dosage forms of this invention are dictated by and are directly dependent on (a) the unique characteristics of the active ingredient and the particular therapeutic effect to be achieved, and (b) the limitations inherent in the art of compounding such an active ingredient for therapeutic use in humans and animals. Examples of suitable dosage forms in accord with this invention are ophthalmic drops, mucosal inserts, saturated contact lenses and the like, diffusion release implants, segregated multiples of any of the foregoing, as well as solutions and suspensions suitable for injection. A solution, as utilized herein, is a liquid homogeneous mixture where a solid or liquid form of the active ingredient is distributed throughout the carrier.

The active ingredient utilized in practicing the present invention is 17-alpha-methyl-testosterone(17-hydroxy-17-methylandrost-4-en-3-one) and is represented by the formula

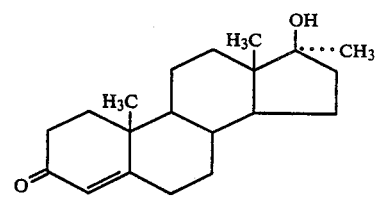

The amount of active ingredient that is to be administered depends on the age of the patient, duration of the disease state, the particular condition to be treated, the frequency of administration, and the route of administration. Additional factors include the degree of elevation of intraocular pressure and/or optic nerve damage, and familial predisposition to glaucoma. The concentration of active ingredient can range from about 0.01 percent to about 10 percent by weight in an ophthalmic solution or an equivalent thereof. Preferred dose is about 0.001 milligram to about 10 milligrams per administration. A more preferred dose is about 0.004 milligram to about 4 milligrams per administration.

The human adult dose for an ophthalmic drop treatment regime is one drop delivering a unit dose in the aforementioned range in each eye in 1 to about 6 daily administrations. Veterinary dosages correspond to human dosages with the amounts administered being in proportion to the weight of the animal as compared to adult humans. The unit dose may be administered in a physiologically tolerable vehicle such as a phosphate buffered saline (PBS) solution.

The concentration of 17-alpha-methyl-testosterone in a particular carrier or vehicle may be adjusted upwardly or downwardly, as required, to accommodate the solubility of any other compatible medication that may be present in the same carrier or vehicle for concurrent administration.

When a pharmacologically effective amount of 17-alpha-methyl-testosterone is topically applied to the conjunctival sac, it is believed to be absorbed through the interstitial spaces of the sclera or cornea by diffusion into the aqueous humor of the eye. The active ingredient thereby is directly absorbed into the trabecular meshwork of the affected eye. This administration regime results in a lowering of intraocular pressure by providing 17-alpha-methyl-testosterone at an elevated concentration in the aqueous humor in contact with the trabecular meshwork for an extended period of time of the order of at least about three days.

The "effective amount" or "pharmacologically effective amount" of active ingredient in a unit dose depends upon a number of factors. Included among those factors are the carrier when used, the tolerance for the active ingredient, the response elicited, and the number of unit dose administrations desired to be used.

In practicing the method of this invention 17-alpha-methyl-testosterone preferably is administered topically so that the concentration of 17-alpha-methyl-testosterone in the aqueous humor in contact with the trabecular meshwork is elevated above its normal concentration in the aqueous humor and 17-alpha-methyl-testosterone can be directly absorbed into the trabecular meshwork of the affected eye.

Affected eyes are those exhibiting elevated intraocular pressure, usually presenting an intraocular pressure of about 21 millimeters Hg or greater as measured with standard tonometric techniques such as Schiotz, MacKay Marg or applanation tonometry. Additional criteria for commencing the prescribed therapy are presentation of the standard diagnostic criteria for primary open angle glaucoma, such as glaucomatous field loss or optic nerve head damage.

The active ingredient contemplated by the present invention can also be administered to the eyes topically in unit dose forms. In such an event, the administered composition comprises a physiologically tolerable carrier and an effective amount of the active ingredient.

The topical instillation or alternate method of administration, sub-Tenon's injection, of 17-alpha-methyl-testosterone avoids metabolic degradation of the biological activity of this drug by systemic digestion or removal of the active compound from systemic circulation by filtering or by metabolic degradation in the liver. Topical instillation or sub-Tenon's injection places the active ingredient in physical proximity to the site of action (the ocular filter mechanism) so that benefical effects may be realized due to constant contact of active ingredient with the ocular filter mechanism (trabecular meshwork). By-products or metabolites of systemically administered 17-alpha-methyl-testosterone are ineffective in the prevention of pharmacologically elevated intraocular pressure, or in the lowering of elevated intraocular pressure perhaps due to low concentration of these substances ultimately directed to the eye via systemic circulation.

According to this invention 17-alpha-methyl-testosterone can also be administered to eyes when there is a risk of induced elevated intraocular pressure, whether from corticosteroid therapy or from some other environmental or pharmacologic substance. Thus, in one aspect the method of this invention may be applied to ameliorate or prevent induced elevated intraocular pressure as well as to treat extant elevated intraocular pressure. The method of invention is also useful to maintain normal or physiologic intraocular pressure.

The contemplated treatment regime of this invention requires application of a pharmacologically effective amount of active ingredient as described, in unit dose form, to an eye presenting elevated intraocular pressure, and maintaining an effective concentration of this active ingredient in the aqueous humor for at least about three days to assure that a lowered intraocular pressure is maintained. For example, intraocular pressure observed six months after a substantially constant physiologic intraocular pressure is obtained may be used as a benchmark to ensure that the affected eye is maintained at physiologic or normal eye pressure. The amount of active ingredient administered to the eye may be decreased after this point, either by decreasing the amount of active ingredient or decreasing the freqency of application of active ingredient in unit dose form to the eye. During this period of adjustment of dosage, the eye should be carefully monitored for any change in intraocular pressure or visual field.

The goal of this therapy regime is to maintain physiologic or normal intraocular pressure. Should it be found that a permanent alteration of the aqueous outflow mechanism is achieved through a biochemical alteration of the trabecular meshwork, such as presently postulated to be a biochemical alteration of metabolism of glycosaminoglycans, and should the patient present such a constant, permanently altered outflow facility, it may be possible to suspend all further treatment. A caveat should be followed in cessation of therapy, that is, regular monitoring of the intraocular pressure and visual field of a previously treated eye should continue throughout the life of the patient. Thus, early detection of any elevated intraocular pressure is possible, and the described treatment regime may again be employed to prevent subsequent glaucomatous visual field loss.

The preferred treatment regime for elevated intraocular pressure commences with about 0.1 mg of 17-alpha-methyl-testosterone administered to the eye approximately four times daily for a time period of at least about three days. As physiologic eye pressure is achieved and maintained, the total daily dose may be decreased to as little as 0.004 mg, or less, as is required to maintain normal intraocular pressure. After one year of maintenance of intraocular pressure at a physiologic level, treatment may be ended and bi-monthly monitoring of intraocular pressure required for a period of six months to ensure that the normal intraocular pressure is maintained. If this desirable condition is continued, monitoring frequency may be decreased, with bi-annual checks of intraocular pressure and visual field continued to ensure that the glaucomatous condition or elevated intraocular pressure does not recur.

The treatment regime contemplated by this invention is effective in maintaining physiologic or normal intraocular pressure. The treatment regime is also effective in reducing elevated intraocular pressure, whether idiopathic or induced by a chemical or pharmacological agent.

It has been shown that an acute administration of anabolic androgenic substances is ineffective in reducing intraocular pressure in a normal eye. This result is anticipated as a normal eye will maintain normal pressure [Lamble, et al., Exp. Eye Res. 26:599–610 (1978)]. That is not the case when an abnormal eye is involved, however.

As shown by the data presented in Table 1, below, 17-alpha-methyl-testosterone was administered to 8 week old New Zealand Red Rabbits presenting normal intraocular pressure. The administration was by instillation into the conjunctaval sac. The dosage was a total of 50 microliters of a 0.1 wt-% or 1.0 wt-% solution of 17-alpha-methyl-testosterone in 100 mM phosphate buffered saline. The treated eyes received a total of 0.02 mg 17-alpha-methyl-testosterone or 0.2 mg 17-alpha-methyl-testosterone.

TABLE 1

Acute Effects of Topical 17-alpha-methyl-testosterone[1]
on IOP[2] of the New Zealand Red Rabbit

| Treatment | n[3] | Time (Minutes) | | | | | |
|---|---|---|---|---|---|---|---|
| | | −30 | 0 | 30 | 60 | 120 | 240 |
| Control | 5 | 24.0 ± 0.7 | 24.0 ± 0.7 | 21.8 ± 1.8 | 22.8 ± 1.3 | 21.6 ± 1.7 | 25.0 ± 1.6 |
| 0.1% 17-alpha-MT | 5 | 24.8 ± 1.3 | 24.2 ± 1.6 | 21.2 ± 1.3 | 22.4 ± 1.9 | 21.6 ± 2.4 | 23.6 ± 1.9 |
| Control | 5 | 23.6 ± 1.5 | 22.4 ± 1.5 | 21.8 ± 2.9 | 21.4 ± 2.8 | 19.6 ± 1.1 | 21.8 ± 2.3 |
| 1.0% 17-alpha-MT | 5 | 23.2 ± 0.8 | 22.4 ± 1.5 | 21.0 ± 2.3 | 21.6 ± 1.5 | 21.0 ± 2.1 | 23.4 ± 1.7 |

[1]Topical administration of one application (50 microliters) of 17-alpha-methyl-testosterone (17-alpha-MT) in 100 mM phosphate-buffered saline, pH 7.4, instilled in the conjunctival sac of 8-week-old New Zealand Red Rabbit eyes at time 0.
[2]Intraocular pressure (IOP) was measured with an Alcon Applanation Pneumatonograph and is expressed as the mean ± the standard deviation before (time −30 minutes), at the time of application (time 0), and at 30, 60, 120 and 240 minutes.
[3]n = number of eyes tested.

Measurements of intraocular eye pressure were taken with an applanation pneumatonograph and showed no statistically significant change in intraocular pressure at any interval of measurement.

It has also been shown by Knepper et al., Exp. Eye Res. 27:567 (1978), that young New Zealand Red Rabbits respond to intraocular pressure elevating compounds when these compounds are administered to the eyes of the subject animals over a period of time. However, the acute administration (single dose) of 17-alpha-methyl-testosterone has no observable intraocular pressure lowering effects in these animals. Thus, constant contact or repeated administration of the active ingredient for an extended time period is necessary to achieve a lowering of elevated or non-physiologic intraocular pressure.

In particular, no lowering of the animals' intraocular normal pressure was observed as a result of an acute contact with active ingredient. This result is consistent with the thesis that a single administration of active ingredient has no effect on intraocular pressure (see Lamble, supra). On the other hand, continuous or repeated administrations of active ingredient provide an unexpected, beneficial effect upon elevated (pathologic) intraocular pressure.

Table 2, below, shows the effect on intraocular pressure of an acute sub-Tenon's administration of 17-alpha-methyl-testosterone on New Zealand Red Rabbits presenting normal intraocular pressure. Again, there were no effects measured in the acute administration. In this instance, 8 week old New Zealand Red Rabbits received one injection beneath Tenon's capsule in the superior nasal and inferior temporal quadrants, a 50 microliter injection of 0.4 mg 17-alpha-methyl-testosterone or 4 mg 17-alpha-methyl-testosterone, with controls receiving an equal volume amount of phosphate buffered saline.

pressure. All eyes tested presented normal pressure before the beginning of the acute studies, and at the conclusion of the studies. Thus, an acute or one-time administration of the active ingredient was of no effect in lowering the intraocular pressure of normal eyes. As will be seen in the examples presented hereinbelow, however, repeated administrations are necessary before therapeutic effect is seen. Affected eyes require at least about three days of administration of 17-alpha-methyl-testosterone before elevated intraocular pressure is reduced, whereas no reduction of normal intraocular pressure occurs as an effect of administration of active ingredient. Concurrent administration of the active ingredient with an intraocular pressure elevating compound maintains normal intraocular pressure, however.

Application of 17-alpha-methyl-testosterone to dexamethasone-treated eyes also reduces elevated intraocular pressure induced by corticosteroid treatment. When a selected anabolic androgen is applied to the eye concurrently with dexamethasone, elevated intraocular pressure does not occur. In the latter instance, the proposed treatment regime comprises concurrent administration of an effective unit dose of the anabolic androgenic compound concurrently with the intraocular pressure elevating compound. This treatment may be halted when the pressure elevating compound has been metabolically removed completely from the affected individual's systemic or ocular circulation.

Suitable pharmacologic carriers for 17-alpha-methyl-testosterone are an aqueous solution, oil suspension, lanolin petrolatum ointment or solid insert such as is commercially available under the designation such as an Ocusert ® by (Ciba Pharmaceutical Co., Summit, N.J.). Ophthalmic solutions may contain 17-alpha-methyl-testosterone in an amount in the range of about 0.01 percent to 10 percent by weight. In the most preferred embodiment, 17-alpha-methyl-testosterone is present in

TABLE 2

Acute Effects of SubTenon's Injection of 17-alpha-methyl-testosterone[1]
on IOP[2] of the New Zealand Red Rabbit

| Treatment | n[3] | Time (Minutes) | | | | | |
|---|---|---|---|---|---|---|---|
| | | −30 | 0 | 30 | 60 | 20 | 240 |
| Control | 4 | 25.0 ± 2.2 | 23.0 ± 2.0 | 23.8 ± 3.0 | 21.8 ± 1.3 | 22.8 ± 2.6 | 23.3 ± 3.3 |
| 1% 17-alpha-MT | 4 | 25.3 ± 2.2 | 23.5 ± 1.3 | 23.3 ± 3.8 | 22.3 ± 1.5 | 23.5 ± 2.6 | 23.5 ± 3.9 |
| Control | 4 | 23.8 ± 1.0 | 22.5 ± 0.6 | 22.5 ± 1.0 | 21.3 ± 2.5 | 22.3 ± 2.2 | 24.0 ± 1.2 |
| 10% 17-alpha-MT | 4 | 23.8 ± 1.0 | 22.3 ± 2.2 | 23.5 ± 1.3 | 21.3 ± 1.3 | 21.3 ± 2.4 | 24.3 ± 1.5 |

[1]The 17-alpha-methyl-testosterone (17-alpha-MT) treated eye received one injection beneath Tenon's capsule of 50 microliters of a 1% suspension or a 10% suspension of 17-alpha-methyl-testosterone dissolved in 100 mM phosphate-buffered saline, pH 7.4, in two quadrants of one eye, superior nasal and inferior temporal quadrants, of 8-week-old New Zealand Red Rabbits. The control eye received the same number and volume of injections of 100 mM phosphate-buffered saline, pH 7.4
[2]Intraocular pressure (IOP) was measured with an Alcon Applanation Pneumatonograph and is expressed as the mean ± the standard deviation before (time −30 minutes), at the time of application (time 0), and at 30, 60, 120, and 240 minutes.
[3]n = number of eyes tested.

As in the case of the data of Table 1 discussed above, there were no observable effects upon the intraocular an amount of about 0.1 percent to 5 percent by weight.

The method of administration for this aspect of the present invention involves suspending the active ingredient in an appropriate carrier, or utilizing a subconjunctival injection of the active ingredient, or sub-Tenon's injection of the active ingredient, or introducing it in any other convenient way such that the active ingredient, 17-alpha-methyl-testosterone, contacts the cornea of the eye where it is absorbed directly into the aqueous humor of the eye, thereby contacting the filter mechanism of the eye. A subconjunctival injection can be formulated utilizing an oil suspension to ensure slow release of the active ingredient over an extended time period. In this instance, a saturated solution or a suspension of the active ingredient forms the major constituent of the composition.

The active ingredient passes through the cornea and sclera by diffusion, acting on the trabecular meshwork whereupon beneficial modification of the rate of aqueous humor outflow is effected. For example, a saturated contact lens allows controlled continuous release of the active ingredient. Thus, a contact lens saturated with 17-alpha-methyl-testosterone allows continuous administration of the active ingredient. A systemic administration of the active ingredient has no ophthalmic effect due to systemic metabolic degradation; however, a controlled release device directly into the eye avoids the metabolic degradation resulting from parenteral or intramuscular administration.

In addition to the preferred saturated contact lens, several other methods of ophthalmic administration are possible. Any route of ophthalmic administration that ensures that the active ingredient diffuses through the cornea thereby reaching the trabecular meshwork can be used. These routes of administration include suspending the compound in a liquid carrier with the appropriate pH such as an isotonic aqueous sodium chloride vehicle, conventional phosphate buffer vehicle systems, isotonic sodium borate vehicle systems, or the like, and applying the active compound directly to the cornea and sclera of the eye by instilling drops into the conjunctival sac. These methods include use of ophthalmic ointments, solutions, subconjunctival injection of a suspension of the active ingredient, sub-Tenon's injection of a suspension of the ingredient, or solid inserts to effect continuous controlled release of the active ingredient.

The pharmaceutical preparation may also contain additional components such as emulsifying, preserving, wetting and sterilizing agents. The carrier that the selected anabolic androgenic substance is suspended in possesses no known intrinsic pharmacological activity.

A particularly preferred route of administration utilizes a contact lens system as the carrier. In this manner, 17-alpha-methyl-testosterone is topically administered to the cornea continuously while vision is unimpaired. Administration of the active ingredient is uninterrupted in contradistinction to treatment regimes that specify the instillation of drops. A saturated contact lens contains a relatively concentrated amount of 17-alpha-methyl-testosterone to assure that a sufficient amount of the active ingredient reaches the trabecular meshwork over a predetermined extended time period of continuous administration.

Another preferred route of administration is a mucosal insert. This device is placed in the subconjunctival sac and operates in a manner similar to the active ingredient-saturated contact lens.

A variety of treatment regimes are therefore possible.

17-alpha-methyl-testosterone is particularly useful for the treatment of primary open angle glaucoma and corticosteroid inducedoocular hypertension or prevention of induced (secondary) elevated intraocular pressure since the compound diffuses directly through the cornea and sclera to alter the trabecular meshwork of the eye, thereby facilitating physiologic aqueous humor outflow resulting in normal intraocular pressure.

The preferred embodiment to be utilized in this invention requires a determination that the eye presents clinical findings, as determined by standard methods, indicating glaucoma. These findings include non-physiologic or abnormal eye pressure, optic nerve damage or visual field loss, whether induced by corticosteroid administration or resulting from spontaneous primary open angle glaucoma. The affected eye is then treated with a solution of 17-alpha-methyl-testosterone at prescribed intervals over a predetermined period of time. The active ingredient is suspended in an appropriate carrier and instilled into the affected eye utilizing an ophthalmic drop, or another instillation method such as injection beneath Tenon's capsule, and administered at such intervals so that the prescribed dosages yield consistent reduction in intraocular pressure.

The following examples more fully illustrate the invention. These examples are intended to be illustrative and are not to be taken as limiting.

EXAMPLE 1

New Zealand rabbits received 0.1 percent dexamethasone solution instilled into both eyes at 6 hour intervals for a period of two weeks. Dexamethasone administration resulted in an increase of intraocular pressure in both eyes of the rabbit (corticosteroid induced glaucoma). Following two weeks of dexamethasone administration in both eyes, the right eye of the rabbits received a treatment regime consisting of a 1.0 percent 17-alpha-methyl-testosterone, in a phosphate buffered saline solution and a 0.1 percent dexamethasone solution administered concurrently whereas the left eye received a 0.1 percent dexamethasone solution alone. Following the concurrent administration of the 17-alpha-methyl-testosterone and dexamethasone solutions, the elevated intraocular pressure in the treated eye was returned to normal levels.

The dexamethasone and 17-alpha-methyl-testosterone solutions were administered alone or concurrently by the topical instillation of one drop of one or both solutions (about 0.04 ml) to each eye about every 6 hours for 4 weeks. A sterile, isotonic phosphate buffer suspension of 17-alpha-methyl-testosterone is prepared by dissolving 1.0 gram in 100 ml of the phosphate buffer to give a 1% solution. A commercial preparation of 0.1% dexamethasone commonly available under the trade name Decadron ® (Merck, Sharp & Dohme, West Point, Pa.) was used to increase ocular hypertension as described by Knepper, P. A., et al., Exp. Eye Res., 27:567 (1978). The test results are shown in Table 3, below.

TABLE 3

| INTRAOCULAR PRESSURE+ MEASUREMENT: Dexamethasone/17-alpha-methyl-testosterone | | |
|---|---|---|
| Week of Treatment | Right Eye° | Left Eye° |
| 0 | 20.0 ± 1.9 | 20.7 ± 1.8 |
| 1 | 21.4 ± 1.3 | 21.1 ± 1.3 |
| 2 | 30.0 ± 5.2 | 28.9 ± 4.5 |
| 3 | 23.6 ± 1.5 | 31.0 ± 4.2 |

TABLE 3-continued

Eye Res. 27:567 (1978). The observed results are presented in Table 4, below.

TABLE 4

Intraocular Pressure+ Measurement and 17-alpha-methyl-testosterone

| Treatment | n | Weeks of Treatment | | | | |
|---|---|---|---|---|---|---|
| | | 0 | 1 | 2 | 3 | 4 |
| Control | 82 | 19.3 ± 1.3 | 19.3 ± 1.0 | 19.2 ± 1.1 | 19.0 ± 1.0 | 18.0 ± 0.9 |
| Dexamethasone, alone° | 138 | 18.7 ± 1.5 | 19.0 ± 2.0 | 23.9 ± 2.8$^{a,b}$ | 25.5 ± 2.6$^{a,b}$ | 26.8 ± 3.2$^{a,b}$ |
| 17-alpha-methyl-testosterone, alone | 62 | 19.3 ± 1.1 | 19.1 ± 1.1 | 19.1 ± 0.9 | 18.9 ± 1.0 | 18.7 ± 1.0 |
| 17-alpha-methyl-testosterone-Dexamethasone, in combination | 42 | 19.6 ± 1.8 | 20.5 ± 1.3 | 20.8 ± 1.7 | 21.2 ± 2.2 | 20.8 ± 3.7 |

Table entries are the mean intraocular pressure mm Hg ± standard deviation.
+Intraocular pressure was measured by MacKay-Marg tonometry.
°Steroid or control (phosphate buffer, 67 mM, pH 7.4) were administered by the topical instillation of ophthalmic drop every 6 hours for 4 weeks.
n = Number of eyes tested.
$^a$p less than 0.001 when compared to the control values.
$^b$p less than 0.001 when compared to the dexamethasone-17-alpha-methyl-testosterone values.

INTRAOCULAR PRESSURE+ MEASUREMENT:
Dexamethasone/17-alpha-methyl-testosterone

| Week of Treatment | Right Eye° | Left Eye° |
|---|---|---|
| 4 | 21.1 ± 1.8$^{a,b}$ | 31.0 ± 4.1 |

Table entries are the mean intraocular pressure, mm Hg, ± the standard deviation for seven rabbit eyes.
+Intraocular pressure was measured by MacKay-Marg tonometry.
°The right eye received 0.1 percent dexamethasone ophthalmic drop alone every 6 hours for 2 weeks and then was treated with 1.0% 17-alpha-methyl-testosterone-0.1% dexamethasone ophthalmic drop of each every 6 hours for 2 weeks. The left eye received 0.1 percent dexamethasone ophthalmic drop alone every 6 hours for 4 weeks.
$^a$p less than 0.001 when compared to 2 week right eye value.
$^b$p less than 0.001 when compared to 4 week left eye value.

The validity of the tonometer measurements performed on the experimental animals to determine intraocular pressure was evaluated by a closed and an open manometric system. The tonometer was highly reliable; the goodness of fit ($r^2$) being 0.963 (closed) and 0.940 (open) with intraocular pressure up to 60 mm Hg for control eyes, 0.887 and 0.958 for eyes treated 2 weeks with dexamethasone, and 0.893 and 0.755 for eyes treated 4 weeks with dexamethasone. In addition, the results of tonometry recordings with a pneumatonograph method were similar to results with the MacKay-Marg method. The results of these studies indicate that the topical administration of dexamethasone induces ocular hypertension in the experimental animals utilized, young New Zealand rabbits, whereas the administration of 17-alpha-methyl-testosterone reverses this effect.

EXAMPLE 2

Normal New Zealand Red Rabbits (10 weeks of age; 1.4 to 1.9 Kg) were treated with 17-alpha-methyl-testosterone and dexamethasone in combination, dexamethasone alone, or a control solution (isotonic saline solution). The dexamethasone and 17-alpha-methyl-testosterone solutions, alone or in combination, were administered by the topical instillation of one drop of one or both compounds (about 0.04 ml) to each eye about every 6 hours for 4 weeks. The sterile, isotonic phosphate buffer suspension of 17-alpha-methyl-testosterone administered to the rabbits was prepared by dissolving 1.0 gram in 100 ml of the phosphate buffer to give a 1% solution. A commercial preparation of 0.1% dexamethasone (Decadron®), was used to increase ocular hypertension as described by Knepper, P. A., et al., Exp.

The result of 17-alpha-methyl-testosterone administration in conjunction with dexamethasone administration was that the intraocular pressure was unaffected in eyes receiving the anabolic androgen and the corticosteroid. This is in contrast to the marked elevation in intraocular pressure found in the dexamethasone administration without the 17-alpha-methyl-testosterone. From these results it can be seen that 17-alpha-methyl-testosterone effectively blocked the adverse reaction to dexamethasone. Additionally, there was a slight decrease in intraocular pressure of 62 eyes treated with 17-alpha-methyl-testosterone alone and a marked increase in intraocular pressure of 5 mm Hg or more in 114 of 138 eyes treated with dexamethasone alone. Intraocular pressure remained unchanged in the eyes treated with dexamethasone and 17-alpha-methyl-testosterone concurrently, effectively blocking the intraocular pressure elevating effect of dexamethasone alone. Thus, the concurrent administration of dexamethasone plus 17-alpha-methyl-testosterone had no effect on intraocular pressure indicating that the anabolic androgenic compound blocked or prevented corticosteroid induced elevated intraocular pressure.

EXAMPLE 3

New Zealand Red Rabbits received weekly sub-Tenons injections of 50 microliters of an 8 mg/ml suspension of dexamethasone acetate (Decadron-LA®, Merck, Sharp & Dohme, West Point, Pa.) in the superior nasal and inferior temporal quadrants of both eyes. Following two weeks of dexamethasone administration in both eyes, the intraocular pressure was found to be elevated. One eye of the rabbits then received a treatment regime consisting of a weekly sub-Tenon's injection of 50 microliters of 100 mg/ml suspension of 17-alpha-methyl-testosterone dissolved in 100 mM phosphate buffered saline, pH 7.4, in two quadrants of the right eye, inferior nasal and superior temporal, administered concurrently with the dexamethasone injections.

Following the concurrent administration of the 17-alpha-methyl-testosterone and dexamethasone acetate solutions, the elevated intraocular pressure in the treated eyes was returned to normal levels.

A sterile, isotonic phosphate buffer suspension of 17-alpha-methyl-testosterone is prepared by dissolving one gram in 10 ml phosphate buffered saline to give an 10 percent solution (100 mg/ml solution). A preparation of 0.1% dexamethasone acetate was obtained commercially (Merck, Sharp & Dohme). The results are shown in Table 5, below.

TABLE 5

Chronic Effects of SubTenon's Injection of 17-alpha-methyl-testosterone on IOP[+] in Steroid-Induced Ocular Hypertension in the Rabbit Eye

| Time (Weeks) | Dexamethasone Acetate Treating Eyes[°] | Dexamethasone Acetate + 17-alpha-methyl-testosterone Treated Eyes[*] |
|---|---|---|
| Baseline | 21.8 ± 1.3 | 21.2 ± 1.6 |
| 1 | 25.8 ± 1.6 | 26.2 ± 1.9 |
| 2 | 27.8 ± 1.3 | 28.6 ± 1.3 |
| 3 | 27.6 ± 2.1 | 26.0 ± 1.7 |
| 4 | 25.2 ± 2.9[z] | 22.0 ± 2.9[a,b] |

Table entries are the mean intraocular pressure, mm Hg ± the standard deviation, for five rabbit eyes.
[+]Intraocular pressure was measured by an Alcon Applanation Pneumatonograph using a topical anesthetic, one ophthalmic drop of 0.5% proparacaine.
[°]The dexamethasone acetate treated eyes received weekly subTenon's injections of 50 microliters of an 8 mg/ml suspension of dexamethasone acetate (Decadron-LA ®, Merck Sharp & Dohme) in two quadrants of each eye - superior nasal and inferior temporal.
[*]The dexamethasone acetate + 17-alpha-methyl-testosterone treated eyes received weekly injections of 50 microliters of an 8 mg/ml suspension of dexamethasone acetate (Decadron-LA ® Merck Sharp & Dohme) in two quadrants of each eye - superior nasal and inferior temporal, and after the second week of treatment with dexamethasone acetate, weekly subTenon's injections of 50 microliters of 100 mg/ml suspension of 17-alpha-methyl-testosterone dissolved in 100 mM phosphate-buffered saline, pH 7.4, in two quadrants of one eye - inferior nasal and superior temporal.
[a]p less than 0.001 when compared to the second week of treatment (dexamethasone alone).
[b]p less than 0.001 when compared to the fourth week of treatment (dexamethasone alone).

Thus it was shown that the intraocular pressure elevating effects of corticosteroids such as dexamethasone acetate can be effectively blocked, as was shown in Example 2, by the concurrent administration of 17-alpha-methyl-testosterone. In this example, the route of administration was identical for both compounds.

EXAMPLE 4

M. fasicularis monkeys received weekly subTenons injections of 50 microliters of an 8 mg/ml suspension of dexamethasone acetate in the superior nasal and inferior temporal quadrants of the eye to induce elevated intraocular pressure. Following four weeks of administration of dexamethasone acetate in both eyes, the intraocular pressure increased to unphysiologic levels. This increase in intraocular pressure was maintained for a period of four weeks.

After elevated intraocular pressure was reduced, one eye received weekly injections of 17-alpha-methyl-testosterone administered to the inferior nasal and superior temporal quadrants of the eye concurrently with dexamethasone acetate injections. The results are shown in Table 6, below.

TABLE 6

Chronic Effects of SubTenon's Injection of 17-alpha-methyl-testosterone[1] on IOP in Steroid-Induced Ocular Hypertension[2] in the Primate Eye

| | Reversing Effects[3] of 17-alpha-MT | |
|---|---|---|
| Time (Weeks) | Right Eye Dexamethasone Acetate | Left Eye Dexamethasone Acetate and 17-alpha-MT |
| Baseline | 28.5 ± 1.0 | 26.8 ± 1.7 |
| 1 | 25 | 24 |
| 2 | 30 | 25 |
| 3 | 30 | 20 |
| 4 | 26 | 19 |

Table entries are the mean intraocular pressure ± the standard deviation. Intraocular pressure was measured by an Alcon Applanation Pneumatonograph after initial sedation using Ketamine (15 mg/kg), Valium ® (Diazepam) Roche Products, Inc., Manati, Puerto Rico, (1 mg/kg), administered intramuscularly and supplements of Ketamine (5 mg/kg) as required.
[1]The 17-alpha-methyl-testosterone (17-alpha-MT) treated eyes received weekly injections of 50 microliters of a 10% suspension of 17-alpha-methyl-testosterone beneath Tenon's capsule in two quadrants of one eye, inferior nasal and superior temporal quadrants, of M. fasicularis monkeys.
[2]Steroid-induced ocular hypertension was produced by weekly injections of 50 microliters of an 8 mg/ml suspension of dexamethasone acetate (Decadron - LA ®, Merck, Sharp & Dohme) beneath Tenon's capsule in two quadrants of one eye, superior nasal and inferior temporal quadrants, of M. fasicularis monkeys.
[3]The reversing effects of 17-alpha-methyl-testosterone are shown in a monkey which was treated for four weeks with weekly injections of dexamethasone acetate in each eye (baseline data) and then treated by weekly injections of 17-alpha-methyl-testosterone in the left eye.

The administration of 17-alpha-methyl-testosterone effectively reversed the intraocular pressure elevating effects of dexamethasone administration.

The validity of the tonometer measurements performed on the experimental animals to determine intraocular pressure was evaluated in a manner similar to Example 1 and found to be highly reliable.

The administration of 17-alpha-methyl-testosterone in conjunction with dexamethasone administration was that the intraocular pressure that was elevated by the administration of dexamethasone acetate was reduced to a physiologic level through the administration of 17-alpha-methyl-testosterone. This is in accordance with the results shown in Example 1 and the dicussion supra.

EXAMPLE 5

M. Fasicularis monkeys received weekly injections of 50 microliters of a 10 percent solution of dexamethasone acetate (Decadron-LA ®, Merck, Sharp & Dohme) beneath Tenon's capsule. Injections were to two quadrants of the eye, the superior nasal and inferior temporal quadrants. The monkeys were monitored, and following two weeks of dexamethasone acetate administration, an elevation of intraocular pressure was noted. Intraocular pressure was allowed to return to normal by cessation of administration of dexamethasone acetate for a period of four weeks.

The intraocular pressure elevating effects of the dexamethasone were blocked by the concurrent administration of 17-alpha-methyl-testosterone. The dexamethasone acetate and 17-alpha-methyl-testosterone were concurrently administered by sub-Tenon's injection. One eye of the monkey received, via sub-Tenon's injection, 17-alpha-methyl-testosterone into the inferior nasal and superior temporal quadrants of one eye, while the other eye received sub-Tenon's injection of dexamethasone acetate alone into the inferior nasal and superior quadrants of the eye. The results are shown in Table 7. The intraocular pressure was measured using an Alcon Applanation Pneumatonograph after initial sedation of the animal using Ketamine (15 mg/kg), Valium ® (diazepam) (1 mg/kg), administered intramuscularly and supplements of Ketamine (5 mg/kg) as required. The validity of the tonometer measurements performed on the experimental animals to determine intraocular pressure was evaluated by a closed and an open manometric system. The results are shown in Table 7, below.

TABLE 7

Chronic Effects of SubTenon's Injection of 17-alpha-methyl-testosterone[1] on IOP in Steroid-Induced Ocular Hypertension[2] in the Primate Eye Blocking Effects[4] of 17 Alpha-MT

| Time (Weeks) | Right Eye Dexamethasone Acetate | Left Eye Dexamethasone Acetate and 17-alpha-MT |
|---|---|---|
| Baseline | 19.5 ± 1.7 | 19.0 ± 2.0 |
| 1 | 19 | 19 |
| 2 | 27 | 18 |
| 3 | 29 | 21 |
| 4 | 26 | 19 |

Table entries are the mean intraocular pressure ± the standard deviation. Intraocular pressure was measured by an Alcon Applanation Pneumatonograph after initial sedation using Ketamine (15 mg/kg), Valium ® (Diazepam) (Roche Products) (1 mg/kg), administered intramuscularly and supplements of Ketamine (5 mg/kg) as required.
[1]The 17-alpha-methyl-testosterone (17-alpha-MT) treated eyes received weekly injections of 50 microliters of a 10% suspension of 17-alpha-methyl-testosterone beneath Tenon's capsule in two quadrants of one eye, inferior nasal and superior temporal quadrants, of M. fasicularis monkeys.
[2]Steroid-induced ocular hypertension was produced by weekly injections of 50 microliters of an 8 mg/ml suspension of dexamethasone acetate (Decadron - LA ®, Merck, Sharp & Dohme) beneath Tenon's capsule in two quadrants of one eye, superior nasal and inferior temporal quadrants, of M. fasicularis monkeys.
[4]The blocking effects of 17-alpha-methyl-testosterone are shown in a monkey which was treated by weekly injections of dexamethasone acetate in each eye and treated by weekly injections of 17-alpha-methyl-testosterone in the left eye.

The results of these studies indicate that the sub-Tenon's injection of dexamethasone acetate induces ocular hypertension in the experimental animals utilized, M. Fasicularis monkeys, and that the administration of 17-alpha-methyl-testosterone via concurrent sub-Tenon's injection, blocks the intraocular pressure llevating effects of the dexamethasone acetate.

This is in accordance with the results discussed in Examples 2, 3 and 4.

The administration of 17-alpha-methyl-testosterone by instillation or sub-Tenon's injection blocked the effect of the dexamethasone as was seen in Examples 2 and 5. In Example 1, the 17-alpha-methyl-testosterone achieved a reversal of the elevation of the intraocular pressure induced through the administration of dexamethasone. No statistically significant reduction in intraocular pressure was achieved by the administration of 17-alpha-methyl-testosterone alone. Thus, the administration of 17-alpha-methyl-testosterone successfully prevented elevation of the intraocular pressure induced by dexamethasone administration.

The administration of 17-alpha-methyl-testosterone successfully reversed the elevation of intraocular pressure induced by dexamethasone administration. The elevation of intraocular pressure by administration of dexamethasone was of a degree of severity such as may occur in primary open angle glaucoma and as regularly occurs as a result of ocular corticosteroid administration. Glaucoma was induced in these animals due to the unavailability of suitable experimental animals with spontaneously occurring primary open angle glaucoma. It is believed that the pressure lowering effect of 17-alpha-methyl-testosterone will be equivalent in spontaneously occurring or induced or secondary open angle glaucoma in humans.

Likewise, the amount of active ingredient in these illustrative examples may be varied to achieve an effective dose range to obtain an intraocular pressure lowering effect in an affected eye.

The foregoing specification and the Examples are intended as illustrative of the present invention and are not to be taken as limiting. Still other compositions and methods of treatment are possible without departing from the spirit and scope of this invention as will be readily apparent to those skilled in the art.

I claim:

1. A method for reducing elevated intraocular pressure in an eye of a warm blooded animal which comprises contacting the affected eye with an intraocular pressure reducing amount of 17-alpha-methyl-testosterone 1 to about 6 times per day for a time period of at least about three days.

2. The method in accordance with claim 1 wherein the contacting is effected by repeated administration of 17-alpha-methyl-testosterone to the eye at predetermined intervals and in a unit dose of about 0.001 to about 10 milligrams per administration.

3. The method in accordance with claim 2 wherein the unit dose is in a range of about 0.004 to about 4 milligrams.

4. The method in accordance with claim 1 wherein the contacting is effected by injecting an effective amount of 17-alpha-methyl-testosterone in a physiologically tolerable vehicle into a body structure of said animal adjacent to the ocular filter mechanism of said animal.

5. The method in accordance with claim 1 wherein the 17-alpha-methyl-testosterone is injected beneath the Tenon's capsule of the eye.

6. A method of reducing elevated intraocular pressure in an eye of a warm blooded animal which elevated intraocular pressure is caused by administration of an intraocular pressure elevating composition to that animal which comprises contacting the eye with an intraocular pressure reducing amount of 17-alpha-methyl-testosterone substantially concurrently with the administration of said intraocular pressure elevating composition and continuing said contacting until said intraocular pressure elevating composition is no longer administered to the eye.

7. The method in accordance with claim 6 wherein the contacting is effected by repeated administration of 17-alpha-methyl-testosterone to the eye at predetermined intervals and in a unit dose of about 0.001 to about 10 milligrams per administration.

8. The method in accordance with claim 6 wherein the contacting is effected by repeated administration of the 17-alpha-methyl-testosterone to the eye at predetermined intervals and in a unit dose of about 0.004 to about 4 milligrams per administration.

9. The method in accordance with claim 6 wherein the contacting is done by injection of 17-alpha-methyl-testosterone beneath the Tenon's capsule of the eye.

* * * * *

UNITED STATES PATENT AND TRADEMARK OFFICE
CERTIFICATE OF CORRECTION

PATENT NO. : 4,812,448

DATED : March 14, 1989

INVENTOR(S) : Paul A. Knepper

It is certified that error appears in the above-identified patent and that said Letters Patent is hereby corrected as shown below:

Col. 4, line 53, "7-alpha-" should be -- 17-alpha- --.

Col. 5, line 41, "wher" should be -- where --.

Col. 16, line 38, "dicussion" should be -- discussion --.

Signed and Sealed this
Twenty-eighth Day of November 1989

*Attest:*

JEFFREY M. SAMUELS

*Attesting Officer*      *Acting Commissioner of Patents and Trademarks*